(12) United States Patent
Basheer

(10) Patent No.: US 8,551,743 B2
(45) Date of Patent: Oct. 8, 2013

(54) IMMOBILIZED INTERFACIAL ENZYMES OF IMPROVED AND STABILIZED ACTIVITY

(75) Inventor: Sobhi Basheer, Sakhnin (IL)

(73) Assignee: Transbiodiesel Ltd., Shfaram (IL)

(*) Notice: Subject to any disclaimer, the term of this patent is extended or adjusted under 35 U.S.C. 154(b) by 625 days.

(21) Appl. No.: 12/522,389

(22) PCT Filed: Dec. 31, 2007

(86) PCT No.: PCT/IL2007/001630
§ 371 (c)(1),
(2), (4) Date: Sep. 24, 2009

(87) PCT Pub. No.: WO2008/084470
PCT Pub. Date: Jul. 17, 2008

(65) Prior Publication Data
US 2010/0035312 A1    Feb. 11, 2010

(30) Foreign Application Priority Data
Jan. 8, 2007    (IL) .......................................... 180598

(51) Int. Cl.
*C12P 7/64*    (2006.01)
(52) U.S. Cl.
USPC ............................................. 435/134; 514/2
(58) Field of Classification Search
None
See application file for complete search history.

(56) References Cited

U.S. PATENT DOCUMENTS 5,773,266 A * 6/1998 Bosley et al. ................. 435/134
6,528,293 B1   3/2003 Nakajima et al.

FOREIGN PATENT DOCUMENTS

| WO | 94/28118 | 12/1994 |
|---|---|---|
| WO | 95/33047 | 12/1995 |
| WO | 97/01632 | 1/1997 |
| WO | 00/56869 | 9/2000 |

OTHER PUBLICATIONS

Blanco et al.,"Functionalization of mesoporous silica for lipase immobilization characterization of the support and the catalysts", Journal of Molecular Catalysis B: Enzymatic 30: 83-93 (2004).*
Cao, Linqiu, "Immobilised enzymes: science or art?", Current Opinion in Chemical Biology 9: 217-226 (2005).*
Rahman et al., Catalysis Today, 93-95:405-410 (2004). "Immobilisation of lipase from Candida rugosa on layered double hydroxides of Mg/Al and its nanocomposite as biocatalyst for the synthesis of ester."
Mateo et al., Enzyme and Microbial Technology, 40(6):1451-1463 (2007). "Improvement of enzyme activity, stability and selectivity via immobilization techniques."
Noureddini et al., Bioresource Technology, 96(7):769-777 (2005). "Immobilized Pseudomonas cepacia lipase for biodiesel fuel production from soybean oil."
Talukder et al., Biochemical Engineering Journal, 33(1):60-65 (2007). "An improved method of lipase preparation incorporating both solvent treatment and immobilization onto matrix."
Ogino et al., Journal of Bioscience and Bioengineering, 91(2):109-116 (2001). "Enzymes which are stable in the presence of organic solvents."

* cited by examiner

*Primary Examiner* — Anand Desai
(74) *Attorney, Agent, or Firm* — Nixon Peabody LLP

(57) ABSTRACT

Disclosed is a process for the preparation of an interfacial enzyme immobilized on an insoluble support, by providing a bi-phase system comprised of an aqueous buffer solution and at least one first organic solvent; mixing said interfacial enzyme with the bi-phase system provided; adding the support to the obtained mixture and mixing; and isolating from the mixture obtained in the last step the interfacial enzyme immobilized on said support. The produced enzyme is locked in its catalytically active confirmation, and thus exhibits improved activity and stability. Also disclosed are uses of the produced enzymes, particularly in the preparation of biodiesel.

9 Claims, 2 Drawing Sheets

IMMOBILIZED INTERFACIAL ENZYMES OF IMPROVED AND STABILIZED ACTIVITY

CROSS-REFERENCE TO RELATED APPLICATIONS

This application is a 35 U.S.C. §371 National Stage of International Application No. PCT/IL2007/001630 filed on Dec. 31, 2007, which designates the United States, and which claims the benefit of priority under 35 U.S.C. §119(a) of Israel Application No. 180598 filed on Jan. 8, 2007, the contents of which are incorporated herein by reference.

FIELD OF THE INVENTION

The invention relates to immobilized interfacial enzymes, particularly lipases and phospholipases, as well as other hydrolases, having improved activity and stability. The invention also relates to processes for the preparation of such enzymes, and their various industrial and investigational uses.

BACKGROUND OF THE INVENTION

Interfacial enzymes are a class of enzymes that comprised of two domains in their proteinous structure; the first is hydrophilic domain while the second is hydrophobic domain. This unique feature imparts this class of enzymes to favor the interfacial area once present in a two-phase system. Under these conditions, the active conformation is formed where the hydrophilic domain of the enzyme molecules faces the aqueous layer while the hydrophobic domain faces the hydrophobic layer.

Lipases and phospholipases are the most familiar interfacial enzymes that express their catalytic activity once present in an interfacial system. Lipases (triacylglycerol hydrolase E.C. 3.1.1.3) are defined as hydrolytic enzymes that act on the ester linkage in triacylglycerol in aqueous systems to yield free fatty acids, partial glycerides and glycerol. Phospholipases also belong to the class of hydrolytic enzymes, however they cleave favorably and specifically the ester linkage of phospholipids present in aqueous systems, to yield free fatty acids, lysophosholipids, glycerophospholipids, phosphatidic acid and free alcohol, depending on the type of phospholipase.

Lipases and phospholipases are widely distributed among animals, plants and microorganisms. The interest in the industrial application of lipases and phospholipases has been rapidly growing during the last two decades. It has been found that under low water activity this class of enzymes catalyzes their reverse hydrolysis reaction. The reverse catalytic activity of lipases and phospholipase has been widely exploited for the synthesis of valuable compounds that contain ester and amide linkages or other related chemicals containing functional groups such as hydroxyl, carboxylic and amino groups. In particularly, lipases and phospholipases have been utilized for re-forming fats, oils, waxes, phospholipids and sphingolipids to obtain new desired functional properties, and for separating optically active compounds from their racemic mixtures. Of particular interest, the use of interfacial enzymes for the synthesis of unique wax esters and short-chain alkyl esters (biodiesel) will be disclosed herein.

Currently, there are more than 40 different lipases and phospholipases commercially available however only a few of them are prepared in commercial quantities. Some of the most industrially promising interfacial enzymes are derived from *Candida antarctica, Candida rugosa, Rhizomucor miehei, Pseudomonas* sp., *Rhizopus niveus, Mucor javanicus, Rhizopus oryzae, Aspergillus niger, Penicillium camembertii, Alcaligenes* sp., *Burkholderia* sp., *Thermomyces lanuginosa, Chromobacterium viscosum*, papaya seeds, and pancreatin.

Immobilization of enzymes has been described by a vast number of techniques basically aiming at reducing the cost contribution of enzymes in the overall process, facilitate recovery of enzymes from the products and enabling continuous operation of the process. Immobilization techniques are in general divided according to the following:
1. Physical adsorption of enzymes to solid supports, such as silica and insoluble polymers.
2. Adsorption on ion-exchange resins.
3. Covalent binding of enzymes to a solid support material, such as epoxidated inorganic or polymer supports.
4. Entrapment of enzymes in a growing polymer.
5. Confinement of enzymes in a membrane reactor or in semi-permeable gels.
6. Cross-linking enzyme crystals (CLECS's) or aggregates (CLEAS's).

All the aforementioned enzyme immobilization procedures are comprised of the following steps:
1. Dissolving the enzyme in an appropriate buffer system with respect to pH, temperature, type of buffer salts and ionic strength.
2. Adding the solid support into the enzyme solution and mixing for some time till enzyme molecules are immobilized on the solid support.
3. Filtering off the solid support which contains the immobilized enzyme.
4. Washing the support with an appropriate buffer to remove loosely bound enzyme molecules and then drying the solid support.

Interfacial enzymes, mostly lipases have been immobilized following the aforementioned techniques. These offered immobilized enzyme preparations possessing low synthetic activity and/or short operational half-life time. In an attempt to increase the synthetic activity of immobilized lipases and other interfacial enzymes different activation methods have been applied. These methods include:
1. Binding the surface functional groups of enzymes with hydrophobic residues such as fatty acids or polyethylene glycol.
2. Coating the surface of enzymes with surfactants, such as polyol fatty acid esters.
3. Contacting enzymes with hydrophobic supports, typically polypropylene, which have been pretreated with hydrophilic solvents, such as ethanol or iso-propanol.
4. Adding enzyme activators, such as salt solution, glycerol, etc. at low concentration, typically below 1%, into the reaction system.

None of the above mentioned methods yielded satisfactory results with respect to activation, stabilization and cost-effectiveness of immobilized interfacial enzymes for carrying out enzymatic reverse conversions at industrial quantities. Also, it has been reported that most enzymes, when immobilized according to the aforementioned procedure, either loose a significant portion of their synthetic activity or they do not exhibit their full activity performance due to certain constraints imposed by the immobilization procedure. For example, coating lipases and phospholipases with polyol fatty acid esters encountered a serious challenge where lipase molecules were not fully coated with the activator; therefore those enzyme molecules not brought into contact with the activator, remained inactive.

It is therefore an object of this invention to provide a new method for obtaining highly active and stable immobilized interfacial enzymes, in particular lipases and phospholipases for synthetic applications. Of particular interest, these enzymes may be used for the synthesis of wax esters and biodiesel.

It is a further object of the present invention to provide highly active, stable, immobilized interfacial enzymes, for use in various industrial as well as investigational procedures.

These and other objects of the invention will become apparent as the description proceeds.

SUMMARY OF THE INVENTION

The present invention relates to a process for the preparation of an interfacial enzyme immobilized on an insoluble support, comprising the steps of:

(a) Providing a bi-phase system comprised of an aqueous buffer solution and at least one first organic solvent;

(b) Mixing said interfacial enzyme with the bi-phase system provided in step (a);

(c) Adding said support to the mixture of step (b) and mixing;

(d) Isolating from the mixture obtained in step (c) the interfacial enzyme immobilized on said support.

Prior to mixing with the enzyme biphasic solution, said support is optionally washed to remove salts and organic materials, and is then treated with a surfactant dissolved in a second organic solvent.

The insoluble support is capable of binding the interfacial enzyme by adsorption or by covalent binding to functional groups. The support is preferably a porous support which may be organic or inorganic, preferably selected from the group consisting of porous inorganic support such as silica- or alumina-based supports, organic supports such as polymer-based support, wherein said support may optionally contain active functional groups such as epoxy or aldehyde groups, or ionic groups.

In the process of the invention, said first organic solvent is selected from alkanes (such as octane), alcohols (such as n-octanol), aldehydes (such as decanaldehyde) and ketones (such as 2-octanone) and any mixture thereof.

The surfactant is preferably, but not limited to, a sugar fatty acid ester, a polyoxyethylene sugar fatty acid ester or ether, medium- and long-chain alkyl glucoside, phospholipid, polyethylene glycol derivative or quaternary ammonium salt.

The said second organic solvent may be an alkane, preferably n-hexane, an ether, preferably diethyl ether, a ketone, preferably acetone, and an alcohol, preferably iso-propanol, and any mixture thereof.

The interfacial enzyme to be prepared by the process of the invention is preferably a lipase or a phospholipase. Specific non-limiting examples are enzymes derived from *Candida antarctica, Candida rugosa, Rhizomucor miehei, Pseudomonas* sp., *Rhizopus niveus, Mucor javanicus, Rhizopus oryzae, Aspergillus niger, Penicillium camembertii, Alcaligenes* sp., *Burkholderia* sp., *Thermomyces lanuginosa, Chromobacterium viscosum*, papaya seeds and pancreatin.

In another aspect, the invention relates to an interfacial enzyme immobilized on a solid porous support, locked at its active confirmation.

In a preferred embodiment of the immobilized enzyme of the invention, the support is homogenously covered with a surfactant, preferably with a monolayer of said surfactant. The support is capable of binding said enzyme by adsorption or by covalent binding to functional groups, and may be organic or inorganic support, preferably selected from inorganic supports such as silica- and alumina-based supports, organic supports such as polymer-based support, and the support may contain active functional groups such as epoxy or aldehyde groups and ionic groups or said support may be an ion exchange resin.

In the enzyme preparation of the invention, the surfactant is preferably, but not limited to, a sugar fatty acid ester, a polyoxyethylene sugar fatty acid ester or ether, medium- and long-chain alkyl glucoside, phospholipid, polyethylene glycol derivative or quaternary ammonium salt.

The immobilized interfacial enzyme of the invention is preferably a lipase or a phospholipase. Specific examples are enzymes derived *Candida antarctica, Candida rugosa, Rhizomucor miehei, Pseudomonas* sp., *Rhizopus niveus, Mucor javanicus, Rhizopus oryzae, Aspergillus niger, Penicillium camembertii, Alcaligenes* sp., *Burkholderia* sp., *Thermomyces lanuginosa, Chromobacterium viscosum*, papaya seeds and pancreatin.

In a further embodiment, the invention relates to an enzymatic process for the preparation of structured wax esters which contain a surface active component inherent to the raw starting material, comprising the step of reacting a raw wax source with an alcohol in the presence of an immobilized lipase of the invention or prepared by the process of the invention. In this process, the resulting structured wax esters contain a surface-active component inherent to the raw starting material, whereby they possess improved water dispersibility.

In a specific embodiment, the invention relates to a process for the preparation of short-chain alkyl esters of fatty acids, preferably fatty acid methyl esters (biodiesel) comprising stepwise adding methanol to a plant, animal, algal or fish oil or a mixture of at least two of these oils that contain a lipase in accordance with the invention or prepared by the process of the invention, and allowing the reaction to proceed under suitable conditions, until said oil triglycerides are converted to fatty acid methyl esters.

In this process, the plant oil may be, but is not limited to soybean, canola, rapeseed, olive, palm oil, sunflower oil, peanut oil, cotton seed oil, waste cooking oil or any oil triglycerides derived from inedible plant sources.

DETAILED DESCRIPTION OF THE INVENTION

Figure 1:
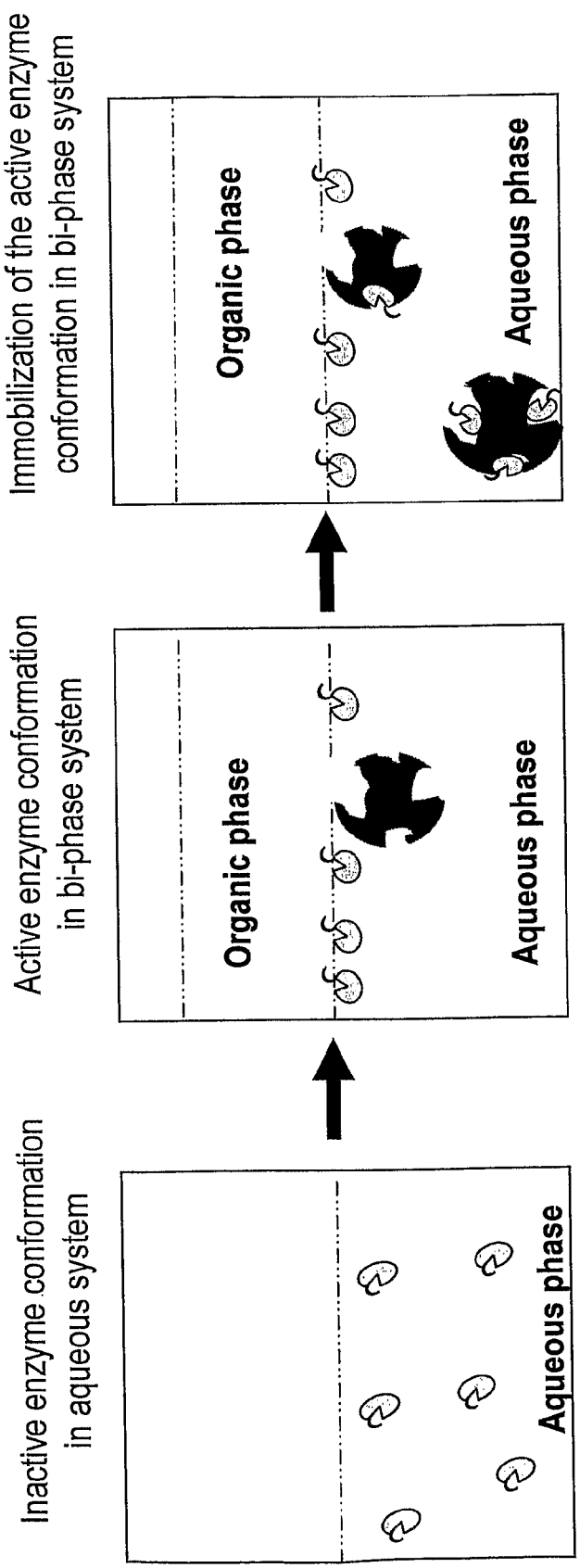
FIG. 1: A schematic illustration of the process for enzyme activation in the interfacial area, followed by enzyme immobilization on a support.

In search for a new method for the preparation of highly active and stable immobilized interfacial enzymes, the present inventor developed a two-step technique, substantially as follows:

Step 1: Forcing all interfacial enzyme molecules to adopt their active confirmation by mixing them in a bi-phase system comprised of aqueous phase and hydrophobic organic phase (see FIGS. 1(A and B).

Step 2: Adding a suitable support into the biphase system which already contains the enzyme (see FIGS. 1(B and C).

The main feature of the support is its capability to position itself in the interface of the bi-phase system.

Under these conditions, the active enzyme molecules which are positioned at the bi-phase interface can be readily immobilized onto the support by simple adsorption, covalent binding with activated resins containing functional groups such as epoxy or aldehyde groups, or by adsorption on ion-exchange resins.

This two-step technique is employed in the preparation of the active immobilized interfacial enzyme in accordance with the invention.

Thus, in a first embodiment, the invention relates to a process for preparing stable, highly active immobilized interfacial enzymes, particularly lipases and phospholipases, in which a bi-phase system comprised of an aqueous buffer solution and at least one first organic solvent is provided; the interfacial enzyme is mixed with the bi-phase system; a solid support is added to the mixture; and the interfacial enzyme immobilized on the support is isolated.

Using specific supports which are characterized with preference to the interfacial area of the bi-phasic system, it "fishes" the enzyme molecules present at the interface, the enzymes thus being locked at their active conformation. The affinity of the support would depend on its porosity, swelling properties as well as dispersibility, which depend on its polarity and on the polarity of the solvent. In a bi-phasic system, hydrophilic supports favor water while hydrophobic supports favor apolar organic solvents.

The present inventor found that in order to improve the affinity of the support to the interfacial area, the surface area of the support, which may be either hydrophilic or hydrophobic, is covered with a mono-layer of a surfactant. This causes the support to favor the interfacial area when present in a bi-phase system. Thus, this feature improves the capability of the support to capture interfacial enzymes "locked" to their active confirmation. Thus, rather than the enzyme diffusing into the support, as known in the art, the present invention provides an efficient tool for fishing the enzyme and stabilizing it to its active confirmation.

Thus, in order to enhance positioning of the solid matrix in the bi-phase interface, the solid matrix, preferably a porous matrix (non-porous matrices can also be used) may be modified, as detailed below, so that it is homogeneously covered with a surfactant. The main feature of the modified support is its tendency to be positioned in the interface produced in hydrophobic-hydrophilic bi-phase systems.

Therefore, in this preferred embodiment, the solid support is pre-treated with a surfactant dissolved in a second organic solvent, before being mixed with the enzyme biphasic solution. Typically, the support which is preferably porous, but can also be non-porous, is first cleaned of any adsorbed salts and organic residues, then dried to remove any water residues, then mixed with a low evaporation organic solvent, e.g. n-hexane, iso-propanol, ethanol, toluene, acetonitrile and like solvents, which contains a surface active agent. The organic solvent is then removed, yielding a dried porous solid support, homogenously covered with the surface active agent. Nonetheless, the process of the invention may be performed also with non-modified (non-pretreated) supports.

The surface active agent (surfactant) may be non-ionic or ionic (anionic or cationic), for example, but not limited to a sugar fatty acid ester, a polyoxyethylene sugar fatty acid ester or ether, a medium- or long-chain alkyl glucoside, a phospholipid, a polyethylene glycol derivative or a quaternary ammonium salt. Specific surfactants are listed in the examples below.

The solid support is preferably a porous support which may be organic or inorganic, particularly selected from the group consisting of porous inorganic supports such as silica- or alumina-based supports, organic supports such as polymer-based support, wherein said support may optionally contain active functional groups such as epoxy or aldehyde groups, or ionic groups. Some specific supports are given in the examples below, particularly in Table 1.

The bi-phasic system is prepared from a suitable aqueous buffer and an organic solvent. This organic solvent may be, but is not limited to, an alkane (such as octane), an alcohol (such as n-octanol), an aldehyde (such as decanaldehyde), a ketone (such as 2-octanone) and any mixture thereof.

Figure 2:
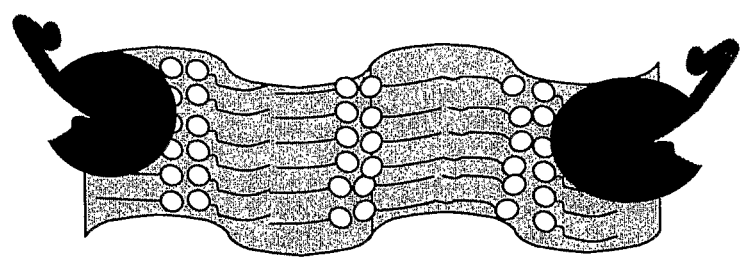
FIG. 2: An interfacial enzyme "locked" to its active confirmation immobilized on a mono-layer surfactant-covered porous support

In a further embodiment, the invention relates to an interfacial enzyme immobilized on a pretreated (modified) solid support which is homogenously covered with a surfactant, preferably with a monolayer of such surfactant. This unique structure enables effective use of the enzyme in reactions that are carried out in organic solvents. The surfactant mono-layer produced on the surface area of the support has a unique structure, represented by head-to-head head groups and tail-to-tail tail groups. A schematic illustration of this structure is shown in FIG. 2. Without being bound by theory, it appears that this structure has a major role with regards to the immobilized enzyme adopting its active and favorable conformation. Also, the surface active agent is attached to the matrix only, preventing de-activation of the enzyme. The enzyme preparation may contain one or more lipases from the group of the enzymes mentioned herein.

The matrices, surfactants and enzymes to be used are as detailed above.

The immobilized enzyme of the invention, or prepared by the method of the invention, is very active, and particularly stable. As can be seen in Table 2 below, activity of about 90% is retained after even 10 cycles of reaction. This stability is of major economic importance.

In another embodiment, the invention relates to a process for preparing structured wax esters, by reacting a wax source with an alcohol in the presence of an immobilized lipase of the invention, or prepared by the process of the invention.

The wax esters obtained by this process contain surface active ingredient/component, which is inherent to the raw starting materials. As shown in the examples below, the molar ratio of oil triglycerides to the alcohol in the reaction system is 1:2, respectively. Hence, the molar ratio between the reaction products, wax esters and monoglycerides inherent to the oil is 2:1, respectively. The alcohol may be any suitable $C_{2-22}$ alkanol, preferably cetyl alcohol. After filtering off the immobilized enzyme, the remaining product contains a mixture of wax esters and monoglycerides at a ratio of 2:1, respectively. Because of the emulsifying properties of monoglycerides, the mixture can be used for the preparation of water-dispersible waxes for use as creams, particularly cosmetic and medical creams, which have improved skin penetration and moisturizing effects. The presence of this surface active agent imparts to the wax esters improved water dispersibility. Thus, the wax esters produced in accordance with the invention are particularly suitable for use as ingredients of various cosmetic and aesthetic products, such as creams and lotions, and can be used as obtained, without the need to add emulsifiers or dispersants. The improved emulsification property of the formed mixture is conferred by the presence of monoglycerides produced in the process. Monoglycerides are well-known as good emulsifiers because the molecule has both hydrophobic and hydrophilic domains, which structure imparts to monoglycerides the ability to improve disperibility of wax esters in water. The wax esters so produced have improved water dispersibility compared to wax esters prepared without using monoglycerides in the same system.

In an important embodiment the invention also relates to a process for the preparation of fatty acid methyl esters (biodiesel). Generally, in this process, methanol is first added step-wise to a plant, animal, algal, fish oil or an oil derived from fungi and contains n-3 or n-6 fatty acids, or a mixture of at least two such oils. A lipase immobilized on a solid support which is covered with a surfactant, preferably a with monolayer of surfactant, or an immobilized lipase prepared by the process of the invention is added to the methanol/oil mixture, and the reaction is allowed to proceed until the oil triglycerides are converted to fatty acid methyl esters.

It is to be noted that in the description herein the terms support and matrix are used interchangingly.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Example 1

Preparation of Immobilized Lipase (Lipozyme TL)

Enzyme support (1 g) is first washed with water to remove any adsorbed salts and organic residues. The support is filtered off and then dried under vacuum to remove water residues. The dried support (1 g) is mixed with organic solvent, such as n-hexane or iso-propanol containing a non-ionic, anionic or cationic surfactant (100 mg). The organic solvent is evaporated under vacuum to yield a dried support covered homogenously with a surfactant (which may be, but are not limited to, phosphatidyl choline, AOT (sodium bis-(2-ethylhexyl)sulphosuccinate), polyethylene glycol, Tween 20, 40, 60, 65, 80 and 85, Span 20, 40, 60, 65, 80, and 85, and sugar fatty acid esters, such as sorbitan mono-, di-, and tri-oleate or other sorbitan fatty acid esters).

Lipase derived from *Thermomyces lanuginosa* (1 ml of Lipozyme TL 100L, Novozymes, Denmark) is mixed in a biphase system comprised of 10 ml phosphate buffer of 0.05 M and pH 6.5, and 10 ml of n-hexane. The mixture is vigorously stirred for 10 min. followed by the addition of surfactant-treated porous support. The mixture is stirred for an additional 4 hours. The support-containing the immobilized enzyme is filtered off and dried in a desiccator overnight to yield the highly active immobilized lipase. The immobilization procedure can be carried out also using non-modified supports.

Table 1 shows the relative transesterification activity of Lipozyme TL 100L immobilized on different supports. Reactions were carried out by adding immobilized lipase (0.5 g) to olive oil (10 g) and cetyl alcohol (5.5 g) (The molar ratio oil triglycerides:cetyl alcohol is 2:1). The reaction system is mixed magnetically or by shaking at 60° C. The conversion of olive oil triglycerides to wax esters was determined after three hours of reaction by calculating the ratio of the sum of the peaks area of olive oil triglycerides after 3 hours of reaction and sum of peaks area of olive oil triglycerides at time zero.

TABLE 1

The conversion (%) of olive oil triglycerides to wax esters after 3 hours of reaction.

| Type of support | Conversion (%) (non-modified support) | Conversion (%) (modified support) |
| --- | --- | --- |
| Amberlite XAD 4 (Rohm&Haas, USA) | 38 | 67 |
| Amberlite XAD 16 (Rohm&Haas) | 23 | 77 |
| Amberlite XAD 7HP (Rohm&Haas) | 24 | 66 |
| Amberlite XAD 16HP (Rohm&Haas) | 30 | 55 |
| Duolite XAD 761 (Rohm&Haas) | 41 | 55 |
| Amberlite XAD 1180 (Rohm&Haas) | 25 | 61 |
| Amberlite XAD 1600 (Rohm&Haas) | 23 | 66 |
| Duolite A7 (Rohm&Haas) | 19 | 52 |
| Duolite A561 (Rohm&Haas) | 18 | 58 |
| Duolite A568 (Rohm&Haas) | 22 | 51 |
| Duolite C467 (Rohm&Haas) | 12 | 22 |
| Amberlyst A-21 (Rohm&Haas) | 19 | 66 |
| Dowex monosphere 77 (DOW, USA) | 32 | 71 |
| Dowex optipore L493 (DOW, USA) | 21 | 51 |
| Dow styrene DVB (DOW, USA) | 14 | 8 |
| MTO Dowex optipore SD-2 (DOW, USA) | 13 | 18 |
| Dowex MAC-3 | 13 | 20 |
| Amberlite FPA53 (Rohm&Haas) | 17 | 31 |
| Amberlite FPC22H (Rohm&Haas) | 11 | 22 |
| Amberlite FPA4OCl (Rohm&Haas) | 32 | 56 |
| AmberliteIRC50 (Rohm&Haas) | 10 | 44 |
| Purolire A109 (Purolite, USA) | 28 | 51 |

Reaction conditions: Olive oil (10 g) and cetyl alcohol (5.5 g) are mixed with lipase TL 100 L immobilized on different supports (0.55 g) for 3 hours. The reaction mixture is shaken at 300 rpm and at 60° C.

When the reaction reaches steady-state conditions, the immobilized enzyme is filtered off to obtain the desired product. The product is comprised of wax esters and monoglycerides inherent to olive oil at a molar ratio of 2:1, respectively. This unique ratio grants the product improved water dispersibility and it can therefore be used for the preparation of cream emulsions, particularly cosmetic or medical creams, with no need for use of external emulsifiers.

Example 2

Immobilized Lipases for the Preparation of Fatty Acid Methyl Esters (Biodiesel)

Different lipases or mixtures of lipases are immobilized according to the above described procedure using various supports. The main lipases that yielded high transesterification activity of methanol and plant oil triglycerides to form fatty acid methyl esters include *Candida antarctica* lipase B (CALB-L Novozymes, Denmark), Lipase QLM (*Alcaligenes* sp. Meito Sangyo, Japan), *Thermomyces lanuginosa* (Lipozyme TL 100L, Novozymes, Denmark), *Pseudomonas* sp. (Lipase PS Amano enzymes, Japan).

The reaction conditions as follows: Soy oil (2.5 g) and methanol (0.3 ml added stepwise 0.1 ml each step within a period of 6 hours of reaction time). The reaction is initiated by adding immobilized lipase (100 mg) and shaking the reaction medium at 35° C. for 6 hours. Table 2 shows the conversion of soybean oil triglycerides to fatty acid methyl esters after 6 hours of reaction time using the same biocatalyst in 10 consecutive cycles.

TABLE 2

The conversion of soybean oil triglycerides to fatty acid methyl esters after 6 hours of reaction time using the same biocatalyst in 10 consecutive cycles.

| Cycle No. | Conversion (%) | | | |
| --- | --- | --- | --- | --- |
| | Lipase TL immobilized on Amberlite XAD 7HP | Lipase QLM immobilized on Amberlite XAD 7HP | Lipase PS immobilized Amberlite XAD 1600 | CALB immobilized on Amberlite XAD 16HP |
| 1 | 90 | 92 | 95 | 60 |
| 2 | 92 | 94 | 96 | 65 |
| 3 | 90 | 92 | 95 | 62 |
| 4 | 92 | 90 | 93 | 67 |
| 5 | 90 | 87 | 92 | 70 |
| 6 | 88 | 90 | 91 | 65 |
| 7 | 87 | 85 | 87 | 66 |
| 8 | 88 | 82 | 90 | 66 |
| 9 | 90 | 82 | 92 | 70 |
| 10 | 89 | 82 | 90 | 67 |

As can be seen from Table 2, most of the activity of the enzyme is retained even after 10 cycles of reaction.

The invention claimed is:

1. A process for the preparation of an interfacial enzyme immobilized on an insoluble support, comprising the steps of:
    (a) providing a bi-phase system comprised of an aqueous buffer solution and at least one first organic solvent;
    (b) mixing said interfacial enzyme with the bi-phase system provided in step (a);
    (c) adding said support to the mixture of step (b) and mixing;
    (d) isolating from the mixture obtained in step (c) the interfacial enzyme immobilized on said support;
    wherein prior to adding said support to the enzyme biphasic solution obtained in step (b), said support is treated with a surfactant dissolved in a second organic solvent, thereby obtaining a support homogenously covered with a monolayer of a surfactant.

2. The process of claim 1, wherein said surfactant is selected from sugar fatty acid esters, polyoxyethylene sugar fatty acid esters or ethers, medium- and long-chain alkyl glucosides, phospholipids, polyethylene glycol derivatives and quaternary ammonium salts.

3. The process of claim 1, wherein said second organic solvent is selected from alkanes, ethers, ketones, alcohols and any mixture thereof.

4. The process of claim 1, wherein said support is optionally washed to remove salts and organic materials, and is then treated with said surfactant.

5. The process of claim 1, wherein said insoluble support is capable of binding said enzyme by adsorption or by covalent binding to functional groups.

6. The process of claim 1, wherein said support is an organic or inorganic porous support selected from the group consisting of silica- or alumina- based porous inorganic supports and polymer-based organic supports, wherein said support may optionally contain active functional groups selected from epoxy groups, aldehyde groups and ionic groups.

7. The process of claim 1, wherein said first organic solvent is selected from alkanes, alcohols, aldehydes and ketones and any mixture thereof.

8. The process of claim 1, wherein said enzyme is a lipase or a phospholipase.

9. The process of claim 8, wherein said enzyme is selected from the group consisting of *Candida antarctica, Candida rugosa, Rhizomucor miehei, Pseudomonas sp., Rhizopus niupsiloneus, Mucor javanicus, Rhizopus oryzae, Aspergillus niger, Penicillium camernbertii, Alcaligenes sp., Burkholderia sp., Thermomyces lanuginosa, Chromobacterium upsiloniscosum*, papaya seeds and pancreatin.

* * * * *

UNITED STATES PATENT AND TRADEMARK OFFICE
CERTIFICATE OF CORRECTION

PATENT NO. : 8,551,743 B2  Page 1 of 1
APPLICATION NO. : 12/522389
DATED : October 8, 2013
INVENTOR(S) : Sobhi Basheer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 702 days.

Signed and Sealed this

Fifteenth Day of September, 2015

Michelle K. Lee
*Director of the United States Patent and Trademark Office*